United States Patent [19]
Weglicki

[11] Patent Number: 6,100,297
[45] Date of Patent: Aug. 8, 2000

[54] INTRAVENOUS MAGNESIUM GLUCONATE FOR TREATMENT OF CONDITIONS CAUSED BY EXCESSIVE OXIDATIVE STRESS DUE TO FREE RADICAL DISTRIBUTION

[75] Inventor: William B. Weglicki, Potomac, Md.

[73] Assignee: The George Washington University, Washington, D.C.

[21] Appl. No.: 09/470,731

[22] Filed: Dec. 22, 1999

Related U.S. Application Data

[60] Continuation of application No. 09/199,938, Nov. 25, 1998, which is a division of application No. 08/787,731, Jan. 24, 1997, Pat. No. 5,843,996.
[60] Provisional application No. 60/011,057, Jan. 25, 1996.

[51] Int. Cl.$^7$ .................................................. A61K 31/19
[52] U.S. Cl. ............................................................. 514/557
[58] Field of Search .............................................. 514/557

[56] References Cited

U.S. PATENT DOCUMENTS

| | | |
|---|---|---|
| 5,871,769 | 2/1999 | Fleming et al. . |
| 5,922,765 | 7/1999 | Fleming et al. . |
| 5,939,394 | 8/1999 | Fleming et al. . |

FOREIGN PATENT DOCUMENTS

97/25959 of 1997 WIPO .

OTHER PUBLICATIONS

Biochemical and Biophysical Research Communications; pp. 1102–1106, vol. 170, No. 3, 1990, Freedman, et al "Magnesium Deficiency–Induced Cardiomyopathy: Protection By Vitamin E".

Molecular and Cellular Biochemistry 110: 169–173, 1992; Weglicki, et al; "Magnesium–deficiency elevates circulating levels of inflammatory cytokines and endothelin".

Antioxidant Characterization and Assay; pp. 620–631; Mak, et al; "Antioxidant Activity of Calcium Channel Blocking Drugs"; Methods in Enzymology, vol. 234 (1994).

Biochemical Pharmacology; vol. 40, No. 9, pp. 2169–2175; 1990; Mak, et al; "Protective Effects of Sulfhydryl–Containing Angiotensin Converting Enzyme Inhibitors Against Free Radical Injury in Endothelial Cells".

Biochemical Pharmacology, vol. 50, No. 9, pp. 1531–1534, 1995; "Protective Effects of Calcium Channel Blockers Against Free Radical–Impaired Endothelial Cell Proliferation"; Mak, et al.

Molecular and Cellular Biochemistry, 000:000–000, 1994, Weglicki, et al; "Neurogenic peptides and the cardiomyopathy of magnesium–deficiency: effects of substance P–receptor inhibition"; pp. 1–7.

Antioxidant Effects of Calcium Channel Blockers Against Free Radical Injury in Endothelial Cells, Correlation of Protection with Preservation of Glutathione Levels, Mak, et al; Circulation Research 70(6), Jun., 1991, pp. 1099–1103.

The FASEB Journal, Abstracts 1–3805; Tutorials T1–T13; Experimental Biology 97; Mak, et al—#396; Apr., 1997.

*Primary Examiner*—James H. Reamer
*Attorney, Agent, or Firm*—Antonelli, Terry, Stout & Kraus, LLP

[57] ABSTRACT

The intravenous use of magnesium gluconate to substantially block free radical surge in the treatment of ischemia/reperfusion (I/R) injury due to oxidative stress.

8 Claims, 2 Drawing Sheets

INTRAVENOUS MAGNESIUM GLUCONATE FOR TREATMENT OF CONDITIONS CAUSED BY EXCESSIVE OXIDATIVE STRESS DUE TO FREE RADICAL DISTRIBUTION

This application claim priority to provisional patent application Ser. No. 60/011,057 filed Jan. 25, 1996.

CROSS REFERENCE TO RELATED APPLICATIONS

This application is a continuation of Ser. No. 09/199,938, filed on Nov. 25, 1998, which application is a divisional of Ser. No. 08/787,731, filed on Jan. 24, 1997 (now U.S. Pat. No. 5,843,996), which application claims priority on provisional patent application Ser. No. 60/011,057, filed on Jan. 25, 1996.

BACKGROUND OF THE INVENTION

It is well established that excessive oxidative stress due to free radicals may injure biological tissues. The natural defenses of cells and tissues revolve around antioxidant mechanisms that have evolved to protect the cells and tissues against high levels of oxidative stress. In our oxygen rich atmosphere the presence of oxygen at certain times of stress may be injurious; this has been termed the oxygen paradox and relates to the role of oxygen in generating and participating in free radical processes. In certain disease states associated with periods of restricted blood flow to tissues, such as heart attack, stroke and restricted flow to the extremities, intermittent episodes of no flow followed by re-flow of blood constitute ischemia/reperfusion (I/R) oxidative stress.

In my laboratory I have utilized cardiac cells such as endothelial cells and cardiomyocytes and their respective membranes as in vitro models to test the susceptibility to free radical stress. I have utilized one of the peptides (glutathione) that is rich in sulfhydryl moieties as an indicator of oxidative stress particularly in the cultured endothelial cell model. In the presence of high levels of superoxide and other radicals glutathione is consumed as a defense against injury to vital membranes. Glutathione is in the cytosol and to some extent in the membrane. I have used Vitamin E or α-tocopherol and other antioxidant agents to provide "first line defense" against excessive radical injury. I have shown that in the presence of these exogenous antioxidant agents the endogenous protective mechanism of glutathione preservation is maintained against levels of oxidative stress that would exhaust the glutathione levels if higher "pharmacological levels" of antioxidants were not present. Thus, this in vitro assay system has enabled us to determine whether an agent has potent antioxidant properties.

Excessive Free Radical Production in Mg-deficiency:

In my studies of dietary deficiency of magnesium in animals we have established that excessive production of free radicals occurs. In these animals one of the first indicators of depletion of normal endogenous levels of antioxidants is seen using the red cell glutathione assay. After just a few weeks on a diet deficient in magnesium we have found significant decreases in red cell glutathione levels. When these animals are supplemented with antioxidants (such as α-tocopherol and antioxidant drugs such as probucol), I have been able to observe protection of a red cell glutathione levels. These studies showed the absence of magnesium resulted in such high levels of free radical production. What seems to be the causal mechanism is that neurological peptides are triggered to be released by low circulating blood levels of magnesium and these in turn trigger production of free radicals by white blood cells, endothelial cells, macrophages and other cells that are capable of responding to neuropeptide stimulation by producing radicals. Further, I have discovered that nitric oxide is produced in excess in these Mg deficient animals; this is another form of a free radical.

Clinical Trials with Magnesium Therapy and Relevant Animal Studies:

In a large investigation, the Second Leicester Intravenous Magnesium Intervention Trial, Woods and colleagues found that giving 2 to 3 grams of magnesium sulfate over first five minutes of presentation and then another 5 grams over the next 24 hours reduced mortality by myocardial infarction at 28 days by 24% and lowered the incidence of left ventricular failure by 25% as reported in Lancet vol. 343, page 1553, 1992.

The Fourth International Study of Infarct Survival (ISIS-4) clinical trials also raised controversy in cardiology with regard to the efficacy of intravenous magnesium administration in patients with acute myocardial infarction.

With the emerging data from the Limit 2 clinical trial and animal studies showing protection of ischemic myocardium, the role of pharmacological levels of magnesium (both clinically as well as in the animal laboratory) came under active investigation. Some of the data showed that mortality was improved in patients who received intravenous magnesium for chest pain (indicating heart attack) in the emergency room. The conclusion of Limit 2 trial was that magnesium given early to patients with infarction was beneficial. The clinical trial by Schecter, et al. *Amer. Heart J.* vol. 132, No. 2, part 2 483–486 (1996) also confirmed the efficacy of magnesium at pharmacological levels when given intravenously to patients having heart attacks. Using animal models Herzog, et al. *Lancet* vol. 343, pages 1285–1286 (1994) provided convincing evidence that magnesium, when present during reperfusion (minute to hour) of previously ischemic myocardial tissue, was protective; indeed, a decrease in the size of the anticipated myocardial infarction was reported in these animal studies. These essential observation of these animal studies (which were more tightly controlled in their design than previous clinical trials such as Limit 2 and ISIS 4) pointed to the protective effect of pharmacological levels of magnesium during the early stage of reperfusion injury. In my previous studies with the isolated perfused rat heart and in the in vivo pig heart, as well as in coronary bypass patients, I have shown a burst of oxygen derived free radicals and free radical derived products in the effluent from hearts perfused after periods of I/R. The earliest burst occurs within seconds to minutes of reperfusion and is not observed beyond 30 minutes of the reperfusion period. The hypothesis that emerged from these observations is that oxygen derived free radicals participate in the I/R injury and that if magnesium at pharmacological levels is able to protect the myocardium during reperfusion it may have an antiradical effect.

Intravenous Therapy with Magnesium:

Clinically Mg sulfate has been utilized for a number of years for patients with toxemia of pregnancy. The intravenous use of Mg sulfate in these patients is efficacious in lowering hypertension which is life threatening in some of these patients. Recent data suggest that the health of the fetus also benefits from magnesium therapy in the peripartum period of time. Another clinical use of intravenous Mg sulfate is in the coronary care unit where patients who have life threatening arrhythmias particularly Torsade de Pointe are given intravenous infusions of Mg sulfate to block these arrhythmias; some of these patients may be deficient in magnesium and repletion is effective in controlling the disordered heart beat. It is curious that only intravenous Mg sulfate is utilized in this country. Other countries have preparations of Mg chloride which can be given intravenously. Early studies by Selye, et al. Amer. Heart J. 55: 163–173 (1958) suggested that Mg sulfate might not be as effective as Mg chloride or other magnesium preparations with different anions. No data exist on Mg gluconate in such clinical studies.

Potential Mechanisms for Cytoprotection by Mg gluconate and Proposed Clinical Efficacy:

The present invention relates to the fact that Mg gluconate has therapeutic efficacy greater than that of Mg sulfate in pathobiological conditions that result from excessive free radical production in vivo. In particular, I/R injury of the myocardium and cerebral tissues is one area of efficacy. Another area is that of cardioplegia at the time of bypass surgery. I/R is also observed in organ preservation; the harvesting of cardiac, renal and hepatic tissues is associated with a prolonged period of no flow or anoxia; prior to implantation in the recipient reinstitution of flow occurs with an oxygenated solution that may result in free radical induced membrane injury. The present invention relates to the use of intravenous Mg gluconate in the early phases of myocardial infarction, bypass cardioplegia, stroke, organ preservation for transplantation and other acute I/R injury conditions. Mg gluconate has greater efficacy than the use of Mg sulfate.

SUMMARY OF THE INVENTION

Briefly, the present invention comprises a method of treating ischemia/reperfusion I/R injury due to oxidative stress by the administration of intravenous magnesium gluconate to a patient in need thereof to substantially block free radical surge in the patient.

It is an object of the present invention to provide a treatment for ischemia/reperfusion injury.

It is another object of the present invention to provide treatment for patients suffering from myocardial infarction.

It is another object of the present invention to provide treatment for patients suffering from stroke.

It is another object of the present invention to provide prevention of reperfusion injury in mammalian tissue that has had its blood flow stopped and reinstituted.

It is another object of the present invention to provide an improved cardioplegic solution for use in bypass surgery.

It is another object of the present invention to provide a method of preserving organs before or after harvesting for transplantation.

These and other objects and advantages will be apparent from the more detailed description which follows.

DETAILED DESCRIPTION OF THE INVENTION

Figure 1:
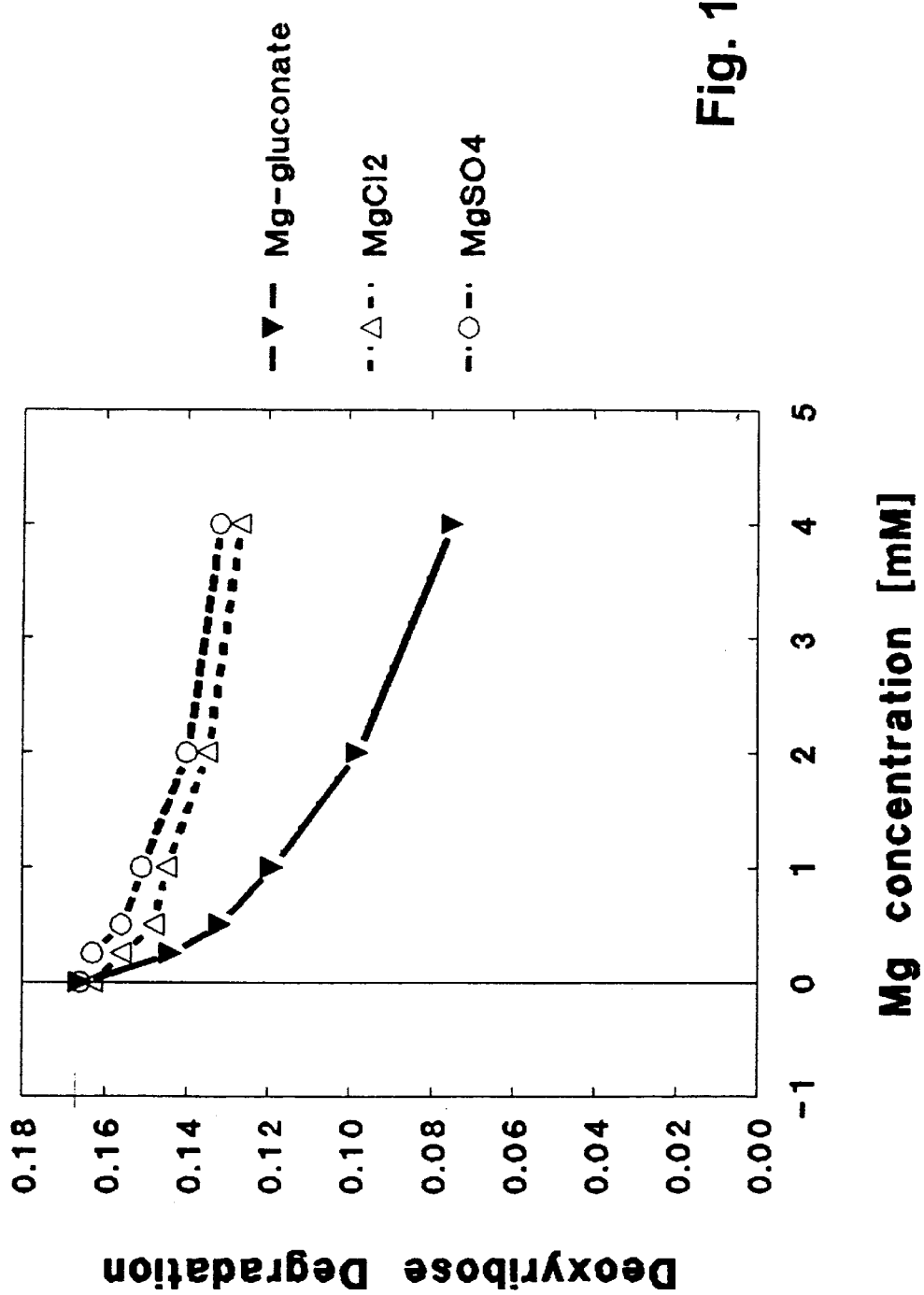
FIG. 1 represents the results of an assay to assess whether or not magnesium sulfate, magnesium chloride or magnesium gluconate would affect the site-specific iron mediated oxidation of deoxyribose.
Figure 2:
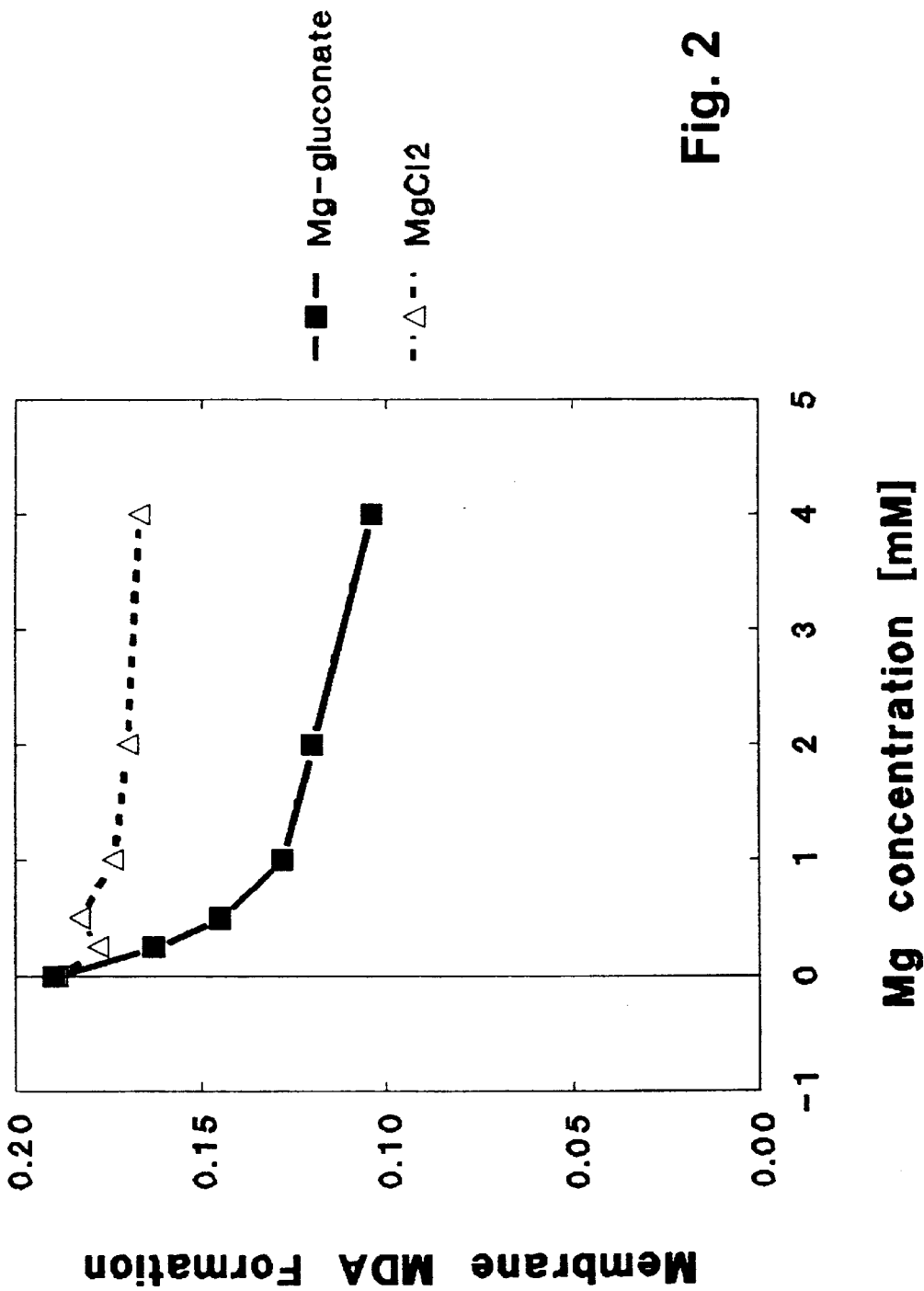
FIG. 2 represents the results of a test wherein magnesium gluconate protects against iron mediated membrane lipid peroxidation.

In accordance with the present invention, magnesium gluconate in a sterile aqueous solution is utilized for the treatment of conditions caused by excessive oxidative stress due to free radical distribution and more specifically, magnesium gluconate, is used in a method of treating ischemia/reperfusion injury.

Ischemia/reperfusion injury is defined as the loss of tissue function or viability due to the sequence of events ensuing after prolonged ischemia (20 minutes or longer) followed by reinstitution of blood flow.

While magnesium has been used in treating myocardial infarction, magnesium gluconate has not. The restoration of blood flow in the infarct-related artery is critical for minimizing necrosis and salvaging myocardium. There is always the risk of possible reperfusion injury. The reperfusion injury may include death of cells that were still viable at the onset of the reperfusion, the no-reflow phenomenon and loss of vasodilator reserve, myocardial stunning and arrhythmias. In accordance with the present invention, magnesium gluconate improves myocardial energy production, inhibits calcium cellular overload, stabilizes injured cell membranes, diminishes free radical induced damage, inhibits intracoronary thrombosis, promotes both coronary and systemic vasodilation and minimizes the development of sinus tachycardia.

The timing of the treatment with magnesium gluconate modulation of reperfusion injury with restoration flow is important. Typically, it should be administered as close to the time of perfusion as feasible. However, it may be administered within about 4 hours after the time of reperfusion.

The dosage of magnesium gluconate for myocardial infarction is defined as that which will elevate the patient's serum level (usually 1.7 to 2.0 mEq/Liter) two-fold to 3.4 to 4.0 mEq/Liter during the first hour of reperfusion, followed by 40 to 60 mmol over the ensuing 24 hours. Generally, the magnesium serum level should be elevated by administeration of magnesium gluconate to about 4 mEq/Liter during the first hour of reperfusion.

There are other methods relating to the preferred embodiments of the present invention.

The method of treating stroke wherein the effective amount of intravenous magnesium gluconate is administered to the stroke victim with the on set of symptoms with continuous dosage for 24 hours as shown above.

The method of preserving an organ for transplantation comprises administering magnesium gluconate to the donar prior to harvest and in the subsequent perfusion solution in an amount to preserve the organ for storage and transplantation and to prevent preimplantation ischemic and reperfusion injury. The amount of the magnesium gluconate needed for preservation is about 40 to 60 mmol over 12 to 24 hours. This dose is generally two times normal level.

The use of magnesium gluconate in a cardioplegic solution for use in cardiac bypass surgery is another embodiment of the present invention. This embodiment includes an adequate and sufficient amount of magnesium gluconate being added to an aqueous solution containing minerals, electrolytes and preservation agents to insure adequate preservation of the heart without reperfusion injury. The amount of magnesium gluconate added to an aqueous solutions of electrolytes and minerals is about 40 meq/Liter of magnesium.

The intravenous route of administration is preferred, however, other routes of administration may be effective, for example, direct infusion into an organ to be preserved for transplantation.

The concentration of the magnesium gluconate should be about 5 to about 10 mmol in sterile water in a 20 ml to 50 ml vial. Such product is commercially available from Sigma Chemical Company, St. Louis, Mo.

The following examples are to illustrate the invention, and are not intended to limit the invention.

EXAMPLE I

Effects of magnesium salts on "site-specific" Fe-mediated deoxyribose oxidation.

This experiment was designed to assess whether or not each of three magnesium salts, magnesium chloride, magnesium sulfate and magnesium gluconate, would affect the "site-specific" Fe-mediated oxidation of the deoxyribose. The procedure was similar to that developed by Gutteridge and Hallivwell (the deoxyribose assay: an assay both for free hydroxyl radical and for site-specific hydroxyl radical production. *Biochem J.* 253: 932–933, 1988). The following ingredients were combined an assay mixture of 1 ml: deoxyribose (1–2.8 mM), $FeCl_3$ (10–20 uM), $H_2O_2$ (2 mM) ascorbic acid (0.1 mM) in a 10 mM potassium phosphate buffer pH 7.4± each magnesium salt (0–4 mM). After 30 minutes of incubation at 30° C. the oxidation product, malondialdehyde, was determined by the thiobarbituric acid method as described in Mak & Weglicki, *Methods Enzymology* 234: 620–630, 1994.

In this assay, iron binds weakly to deoxyribose; in the presence of hydrogen peroxide, hydroxyl radical is generated site-specifically and which oxidizes the deoxyribose. Oxidation of deoxyribose is determined by the accumulation of the degradation product which reacts with thiobarbituric acid to form colored products with absorbance of 532 mM. Results are seen in FIG. 1. The higher the absorbents represented by the Y-axis, the more extensive the oxidation of deoxyribose. Any agent with metal binding capacity would be able to withdraw the deoxyribose-bound iron and inhibit the reaction.

As seen in FIG. 1, of the three magnesium salts, it appears that magnesium gluconate produced the most prominent concentration-dependent inhibition of the deoxyribose oxidation. At 4 mM, magnesium gluconate displayed a 55% inhibition whereas either magnesium chloride or magnesium sulfate at the same concentration only afforded approximately 15% inhibition. magnesium gluconate can function as a more superior "iron-chelator" than $MgCl_2$ or $MgSO_4$.

EXAMPLE II

Effects of Magnesium Salts on $Fe_2$+-mediated membrane lipid peroxidation

This experiment was designed to see if magnesium gluconate would protect against iron-mediated membrane lipid peroxidation. The complete assay procedure in which the microsomal membrane lipid peroxidation was induced by ferrous iron is described in a procedure published by Mak and Weglicki, *JCI* 75: 58–65, 1985. The assay mixture (500 ul) consisted of rat liver microsomal membranes (0.2 mg/ml), ± each magnesium-salt, the chloride, the sulfate, and the gluconate, (0–4 mM), in the 10 mM potassium phosphate buffer, pH 7.4. The lipid peroxidation reaction was initiated by the final addition of 100 uM ferrous sulfate ($FeSO_4$. $7H_2O$). After 20 minutes of reaction at 30° C., the membrane lipid peroxidation was determined by the MDA-TBA method as described in Mak and Weglicki, *Methods of Enzymology* 234: 620–630, 1994. Membrane lipid peroxidation was monitored by malondialdehyde (MDA) formation on the Y-axis. When magnesium gluconate was introduced into the reaction mixture, lipid peroxidation was inhibited to a varying degrees depending upon the magnesium salt concentration. At 4 mM, magesnium gluconate inhibited MDA formation by about 45%, whereas $MgCl_2$ for the entire concentration range did not inhibit more than 10%. The inhibitory effect of Mg-gluconate was primarily due to significant iron-chelating activity which protected the membrane against irion-mediated lipid peroxidation.

What is claimed is:

1. A method of conducting coronary bypass surgery comprising administering an antioxidant cardioplegic solution comprising an effective amount of magnesium gluconate, and minerals and electrolytes, wherein said magnesium gluconate Provides antioxidant properties to said cardioplegic solution.

2. A method of treating oxidative stress in a patient in need thereof, comprising: administering magnesium gluconate in an amount sufficient to reduce oxidative stress and diminish free radical damage to said patient.

3. The method of claim 2, wherein the patient in need thereof is pregnant and has toxemia.

4. A method of treating oxidative stress in a patient in need thereof, comprising: administering magnesium gluconate in an amount sufficient to reduce oxidative stress and diminish free radical damage to cerebral tissues in said patient.

5. The method of claim 4, wherein the patient has had a stroke.

6. A method of stabilizing injured cell membranes in a patient in need thereof, comprising: administering magnesium gluconate in an amount sufficient to stabilize injured cell membranes and reduce oxidative stress in said patient.

7. A method of stabilizing sinus tachycardia and arrhythmia in a patient in need thereof, comprising: administering magnesium gluconate in an amount sufficient to stabilize tachycardia and reduce oxidative stress in said patient.

8. A method of protecting against iron-mediated membrane lipid peroxidation comprising administering magnesium gluconate in an amount sufficient to protect against iron-mediated membrane lipid peroxidation and reduce oxidative stress in said patient.

* * * * *